(12) United States Patent
Liphardt et al.

(10) Patent No.: US 8,749,782 B1
(45) Date of Patent: Jun. 10, 2014

(54) DLP BASE SMALL SPOT INVESTIGATION SYSTEM

(75) Inventors: Martin M. Liphardt, Lincoln, NE (US); Galen L. Pfeiffer, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 475 days.

(21) Appl. No.: 13/199,311

(22) Filed: Aug. 25, 2011

Related U.S. Application Data

(63) Continuation-in-part of application No. 12/806,380, filed on Aug. 11, 2010, now Pat. No. 8,345,241, which is a continuation-in-part of application No. 12/002,650, filed on Dec. 18, 2007, now Pat. No. 7,777,878.

(60) Provisional application No. 60/875,599, filed on Dec. 19, 2006, provisional application No. 61/402,405, filed on Aug. 30, 2010.

(51) Int. Cl.
*G01J 3/28* (2006.01)

(52) U.S. Cl.
USPC .......................................... 356/330; 356/369

(58) Field of Classification Search
CPC . G01N 21/21; G01N 2021/212; G01N 21/47; G01J 3/0237; G01J 3/06; G01J 3/2846; G01J 3/443
USPC ................................ 356/330, 328, 369, 310
See application file for complete search history.

(56) References Cited

U.S. PATENT DOCUMENTS

| | | | |
|---|---|---|---|
| 4,114,366 A | 9/1978 | Renner et al. | 368/68 |
| 5,517,312 A | 5/1996 | Finarov | 356/630 |
| 5,909,559 A | 6/1999 | So | 710/307 |
| 5,932,119 A | 8/1999 | Kaplan et al. | 219/121.68 |
| 5,963,326 A | 10/1999 | Masao | 356/369 |
| 6,028,671 A | 2/2000 | Svetkoff et al. | 356/368 |
| 6,061,049 A | 5/2000 | Pettitt et al. | 345/691 |
| 6,105,119 A | 8/2000 | Kerr et al. | 711/219 |
| 6,163,363 A | 12/2000 | Nelson et al. | 355/32 |
| 6,179,489 B1 | 1/2001 | So et al. | 718/102 |
| 6,200,646 B1 | 3/2001 | Neckers et al. | 427/510 |
| 6,259,153 B1 | 7/2001 | Corisis | 257/666 |
| 6,275,271 B1 | 8/2001 | Hitomi | 348/743 |
| 6,298,370 B1 | 10/2001 | Tang et al. | 718/102 |
| 6,398,389 B1 | 6/2002 | Bohler et al. | 362/293 |
| 6,459,425 B1 | 10/2002 | Holub et al. | 345/207 |
| 6,496,477 B1 | 12/2002 | Perkins et al. | 370/228 |
| 6,558,006 B2 | 5/2003 | Ioka | 353/94 |
| 6,583,921 B2 | 6/2003 | Nelson | 359/291 |
| 6,618,186 B2 | 9/2003 | Kaeriyama | 359/292 |
| 6,619,804 B2 | 9/2003 | Davis et al. | 353/98 |

(Continued)

OTHER PUBLICATIONS

EP 1258288, Houston Univ.

(Continued)

*Primary Examiner* — Tarifur Chowdhury
*Assistant Examiner* — Michael P Lapage
(74) *Attorney, Agent, or Firm* — James D. Welch

(57) ABSTRACT

Computer driven systems and methods involving at least one electromagnetic beam focuser and digital light processor that in combination serve to position selected wavelengths in a spectroscopic electromagnetic beam onto a small spot on a sample, and direct the one or more selected wavelengths reflected by the sample into, while diverting other wavelengths away from, a detector.

15 Claims, 1 Drawing Sheet

(56) References Cited

U.S. PATENT DOCUMENTS

| | | | |
|---|---|---|---|
| 6,654,516 B2 | 11/2003 | So | 385/27 |
| 6,658,063 B1 | 12/2003 | Mizoguchi et al. | 375/260 |
| 6,665,110 B2 | 12/2003 | Pettit | 359/291 |
| 6,741,503 B1 | 5/2004 | Farris et al. | 365/189.05 |
| 6,758,571 B2 | 7/2004 | Heaton | 359/872 |
| 6,781,094 B2 | 8/2004 | Harper | 219/121.72 |
| 6,842,549 B2 | 1/2005 | So | 385/15 |
| 6,856,446 B2 | 2/2005 | DiCarlo | 359/291 |
| 6,857,751 B2 | 2/2005 | Penn et al. | 353/97 |
| 6,870,660 B2 | 3/2005 | DiCarlo | 359/291 |
| 6,897,955 B2 | 5/2005 | Wielsch | 356/369 |
| 6,906,687 B2 | 6/2005 | Werner | 345/8 |
| 7,006,995 B1 | 2/2006 | Edenson et al. | 705/51 |
| 7,011,415 B2 | 3/2006 | DiCarlo et al. | 353/99 |
| 7,019,881 B2 | 3/2006 | Doherty et al. | 359/249 |
| 7,061,512 B2 | 6/2006 | Morgan et al. | 345/691 |
| 7,072,094 B2 | 7/2006 | Mezenner | 359/290 |
| 7,075,643 B2 | 7/2006 | Holub | 356/326 |
| 7,088,486 B2 | 8/2006 | DiCarlo | 359/224 |
| 7,095,498 B2 | 8/2006 | Horie et al. | 356/364 |
| 7,116,489 B2 | 10/2006 | Huffman | 359/239 |
| 7,126,682 B2 | 10/2006 | Rowe et al. | 356/310 |
| 7,149,027 B2 | 12/2006 | Mehrl | 359/290 |
| 7,158,180 B2 | 1/2007 | Neidrich | 348/340 |
| 7,164,397 B2 | 1/2007 | Pettitt | 345/63 |
| 7,187,484 B2 | 3/2007 | Mehrl | 359/290 |
| 7,194,169 B2 | 3/2007 | Ikeda et al. | 385/115 |
| 7,196,740 B2 | 3/2007 | Huibers | 348/744 |
| 7,233,427 B2 | 6/2007 | Doherty et al. | 359/245 |
| 7,236,150 B2 | 6/2007 | Hui | 345/87 |
| 7,245,375 B2 | 7/2007 | Finarov | 356/364 |
| 7,252,395 B2 | 8/2007 | DiCarlo et al. | 353/99 |
| 7,262,817 B2 | 8/2007 | Huiberr | 348/771 |
| 7,265,766 B2 | 9/2007 | Kempf | 345/690 |
| 7,567,345 B1 | 7/2009 | Liphardt et al. | 356/369 |
| 2001/0010843 A1 | 8/2001 | Garner | |
| 2002/0024640 A1 | 2/2002 | Ioka | |
| 2002/0041420 A1 | 4/2002 | Garner | |
| 2002/0057431 A1 | 5/2002 | Fateley et al. | |
| 2002/0081582 A1 | 6/2002 | Gao | |
| 2002/0171834 A1 | 11/2002 | Rowe et al. | |
| 2003/0003032 A1 | 1/2003 | Garner | |
| 2003/0019852 A1 | 1/2003 | Kaplan | |
| 2003/0020703 A1 | 1/2003 | Holub | |
| 2003/0054388 A1 | 3/2003 | Garner et al. | |
| 2003/0062802 A1 | 4/2003 | Battaglin et al. | |
| 2003/0138363 A1 | 7/2003 | Gao | |
| 2003/0143131 A1 | 7/2003 | Gao | |
| 2003/0186427 A1 | 10/2003 | Gao | |
| 2004/0008115 A1 | 1/2004 | Shih et al. | |
| 2004/0023368 A1 | 2/2004 | Gao | |
| 2004/0035690 A1 | 2/2004 | Gulari | |
| 2004/0159641 A1 | 8/2004 | Kaplan | |
| 2005/0001820 A1 | 1/2005 | Lee | |
| 2005/0030328 A1 | 2/2005 | Yamada et al. | |
| 2005/0079386 A1 | 4/2005 | Brown | |
| 2005/0213092 A1 | 9/2005 | MacKinnon | |
| 2005/0251230 A1 | 11/2005 | MacKinnon et al. | |
| 2005/0270528 A1 * | 12/2005 | Geshwind et al. | 356/330 |
| 2006/0019757 A1 | 1/2006 | Brunetti | |
| 2006/0028718 A1 | 2/2006 | Seel et al. | |
| 2006/0038188 A1 | 2/2006 | Erchak et al. | |
| 2006/0134669 A1 | 6/2006 | Casasanta et al. | |
| 2006/0197757 A1 | 9/2006 | Holub | |
| 2006/0220562 A1 | 10/2006 | Tsukamoto | |
| 2010/0106456 A1 * | 4/2010 | Genio et al. | 702/172 |

OTHER PUBLICATIONS

EP 00916981, Max Plancle Gesellschsft zur Forderung.

* cited by examiner

DLP BASE SMALL SPOT INVESTIGATION SYSTEM

This Application is a CIP of Ser. No. 12/806,380 Filed Aug. 11, 2010 and thervia of Ser. No. 12/002,650 Filed Dec. 18, 2007, (now U.S. Pat. No. 7,777,878), from which Benefit of 60/875,599 Filed Dec. 19, 2006 is Claimed. This Application also Claims directly Benefit of Provisional Application 61/402,405 Filed Aug. 30, 2010.

TECHNICAL AREA

The present invention relates to systems and methods of investigating samples with electromagnetic radiation, and more particularly to computer driven systems and methods involving a digital light processor to select known wavelengths in a spectroscopic range thereof, and means for positioning at least one focusing means in synchrony with its operation.

BACKGROUND

As disclosed in U.S. Pat. No. 7,777,878 to Liphardt, it is known to apply digital light processors to select known wavelengths from a spectroscopic range thereof in spectrometers. Additional known references which are also relevant to this are:
Published Application of Fateley et al., No. 2002/0057431;
Published Application of Maurel No. 2004/0155195; and
U.S. Pat. No. 6,663,560 to MacAulay et al.

U.S. Pat. No. 7,508,510 to Pfeifer et al. also discloses that it is known to apply movable focusing means to provide the capability of focusing different wavelengths of electromagnetic radiation onto samples at precisely the same small spot. Discussion of use of a computer to control the positioning of focusing means is also discussed.

What is believed is not disclosed in the prior art is the synchronous combined use of a digital light processor and focusing means to sequentially apply a sequence of wavelengths to precisely the same small spot on a sample.

DISCLOSURE OF THE INVENTION

In a first embodiment, the present invention is a system comprising:
a source (S) of a spectroscopic beam of electromagnetism;
a first focuser (F1);
a stage (STG) for supporting a sample;
optionally a second focuser (F2);
a disperser (DISP);
a digital light processor (DLP);
a third focuser (F3); and
a detector (DET).

Said system further comprises a system for moving said first focuser (F1), optionally a system for moving said second focuser (F2) and a computer (CMP) system for controlling the position of said first focuser (F1) and said optional second focuser (F2) and for operating said digital light processor (DLP) in synchrony therewith. In use a spectroscopic beam of electromagnetic radiation is provided by said source (S) thereof and directed to pass through said first focuser (F1), interact with a small spot on said sample (SS) placed on said stage (STG) for supporting a sample (SS), and then become dispersed by interaction with said disperser (DISP) before being directed onto said digital light processor (DLP). Further in use, said computer (CMP) system causes said first focuser (F1) and optionally said second focuser (F2), via the system for moving said first focuser (F1) and said optional system for moving said second focuser (F2), to be positioned at known distances from said small spot on said sample (SS) so that at least one known wavelength in said spectroscopic beam of electromagnetic radiation is precisely focused onto said small spot on said sample (SS) by said first focuser (F1), and such that said computer also simultaneously operates said digital light processor (DLP) to direct said at least one wavelength into said detector (DET), while diverting other wavelengths away from said detector (DET).

Said system can further comprise a polarization state generator (PSG) and polarization state analyzer (PSA) between said source (S) of a spectroscopic beam of electromagnetism and said stage (STG), and between said stage (STG) and said disperser (DISP), respectively, and the system is an ellipsometer or polarimeter.

It is noted that at least two wavelengths can be simultaneously caused to be focused onto said small spot on said sample (SS) and are caused to be sequentially directed, by said digital light processor, into said detector (DET).

A method of investigating a small spot on a sample (SS) with at least one wavelength in a beam of spectroscopic electromagnetic radiation comprises providing a system as described above, and followed by practicing the steps:

b) causing said source of a spectroscopic beam of electromagnetism to provide a spectroscopic beam of electromagnetism and direct it toward said first focuser (F1);

c) said computer causing said first focuser (F1) and said optional second focuser (F2) to be, via the system for moving said first focuser (F1) and said optional system for moving said second focuser (F2), to be positioned at known distances from said small spot on said sample (SS) so that at least one known wavelength in said spectroscopic beam of electromagnetic radiation is precisely focused onto said small spot on said sample (SS) by said first focuser (F1), and such that said computer also simultaneously operates said digital light processor (DLP) to direct said at least one wavelength into said detector (DET), while diverting other wavelengths which are not precisely focused onto said small spot on said sample (SS) away from said detector (DET).

In a second embodiment the system comprises:
a source (S) of a spectroscopic beam of electromagnetism;
a disperser (DISP);
a digital light processor (DLP);
a first focuser (F1);
a stage (STG) for supporting a sample;
optionally a second focuser (F2); and
a detector (DET).

Said system further comprises system for moving said first focuser (F1), optionally system for moving said second focuser (F2) and a computer (CMP) system for controlling the position of said first focuser (F1) and said optional second focuser (F2) and for operating said digital light processor (DLP) in synchrony therewith. In use said computer (CMP) system causes said first focuser (F1) and optionally said second focuser (F2), via the system for moving said first focuser (F1) and said optional system for moving said second (F2), to be positioned at known distances from said small spot on said sample (SS) so that at least one known wavelength in said spectroscopic beam of electromagnetic radiation is directed by the digital light processor (DLP) and precisely focused onto said small spot on said sample (SS) by said first focuser (F1), and such that said computer also simultaneously operates said digital light processor (DLP) to direct said at least one wavelength toward said first focuser (F1), while diverting other wavelengths away therefrom.

Said system can further comprise a polarization state generator (PSG) and polarization state analyzer (PSA) between said source (S) of a spectroscopic beam of electromagnetism and said stage (STG), and between said stage (STG) and said disperser (DISP), respectively, and the system is an ellipsometer or polarimeter.

A method of investigating a small spot on a sample (SS) with at least one wavelength in a beam of spectroscopic electromagnetic radiation comprises providing a system as just described above, followed by steps:

b) causing said source of a spectroscopic beam of electromagnetism to provide a spectroscopic beam of electromagnetism and direct it toward said disperser;

c) said computer causing said first focuser (F1) and said optional second focuser (F2) to be, via the system for moving said first focuser (F1) means and said optional system for moving said second focuser (F2), to be positioned at known distances from said small spot on a sample (SS) so that at least one known wavelength in said spectroscopic beam of electromagnetic radiation is precisely focused onto said small spot on said sample (SS) by said first focuser (F1), and such that said computer also simultaneously operates said digital light processor (DLP) to direct said at least one wavelength toward said first focuser (F1), while diverting other wavelengths away therefrom;

such that said at least one wavelength interacts with a sample (SS) on said stage (STG) and reflects into said detector (DET).

In both embodiments the system can have only a second focuser (F2) present without the system for moving said second focuser (F2), or both the second focuser (F2) and the system for moving said second focuser (F2) can be present.

In both embodiments said system can further comprise means a system for detecting the intensity of the beam of electromagnetic radiation entering the detector (DET), and in which said computer (CMP) further comprises the capability of causing the digital light processor (DLP) to operate to direct said at least one wavelength into said detector (DET) for a length of time such that the total integrated intensity entering the detector (DET) is of at least a minimum amount.

The present invention will be better understood by reference to the Detailed Description Section of the Specification in combination with the Drawings.

DETAILED DESCRIPTION

Figure 1:
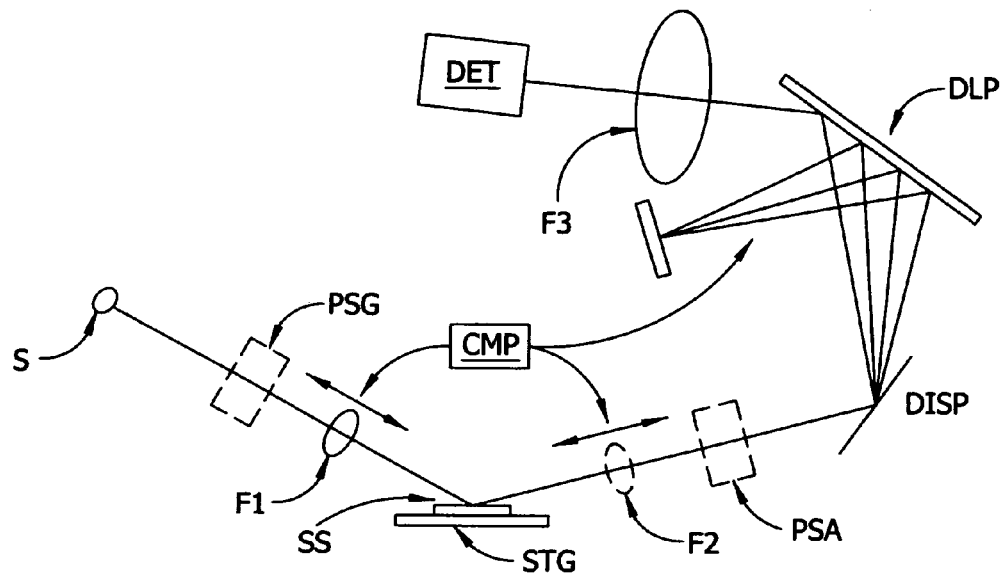
FIG. 1 shows an embodiment of the present invention wherein a digital light processor is present after a sample supporting stage.
Figure 2:
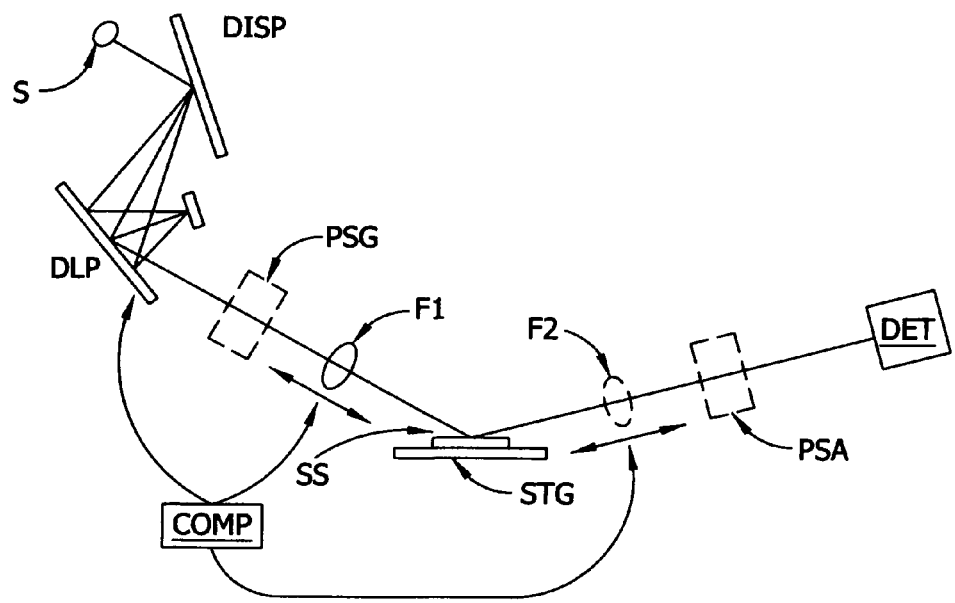
FIG. 2 shows an embodiment of the present invention wherein a digital light processor is present before a sample supporting stage.

Turning now to the Drawings, FIGS. 1 and 2 show the first and second embodiments of the present invention.

Specifically, FIG. 1 shows:
a source (S) of a spectroscopic beam of electromagnetism;
a first focuser (F1);
a stage (STG) for supporting a sample;
optionally a second focuser (F2);
a disperser (DISP);
a digital light processor (DLP);
a third focuser (F3); and
a detector (DET);

in addition to system for moving said first focuser (F1), optionally system for moving said second focuser (F2) and a computer (CMP) system for controlling the position of said first focuser (F1) and said optional second focuser (F2) and for operating said digital light processor (DLP) in synchrony therewith.

In addition FIG. 2 specifically shows:
a source (S) of a spectroscopic beam of electromagnetism;
a disperser (DISP);
a digital light processor (DLP);
a first focuser (F1);
a stage (STG) for supporting a sample;
optionally a second focuser (F2); and
a detector (DET).

in addition to system for moving said first focuser (F1), optionally system for moving said second focuser (F2) and a computer (CMP) system for controlling the position of said first focuser (F1) and said optional second focuser (F2) and for operating said digital light processor (DLP) in synchrony therewith.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system sequentially comprising:
a source (S) of a spectroscopic beam of electromagnetism;
a first focuser (F1);
a stage (STG) for supporting a sample;
provision for mounting a second focuser (F2);
a disperser (DISP);
a digital light processor (DLP);
a third focuser (F3); and
a detector (DET);
said system further comprising a computer (CMP) system for controlling the position of said first focuser (F1), and for operating said digital light processor (DLP) in synchrony therewith;
such that in use a spectroscopic beam of electromagnetic radiation is provided by said source (S) thereof and directed to pass through said first focuser (F1), interact with a small spot on a sample (SS) placed on said stage (STG) for supporting a sample (SS), reflect therefrom and then become dispersed by interaction with said disperser (DISP) before being directed onto said digital light processor (DLP);
and such that in use said computer (CMP) system causes said first focuser (F1), to be positioned at a known distance from said small spot on said sample (SS) so that at least one wavelength in said spectroscopic beam of electromagnetic radiation is focused onto said small spot and such that said computer also simultaneously operates said digital light processor (DLP) to direct said at least one wavelength, after focusing by the third focuser (F3) into said detector (DET), while diverting other wavelengths away from said detector (DET).

2. A system as in claim 1 which further comprises a polarization state generator (PSG) and polarization state analyzer (PSA) between said source (S) of a spectroscopic beam of electromagnetism and said stage (STG), and between said stage (STG) and said disperser (DISP), respectively, and the system is an ellipsometer or polarimeter.

3. A system as in claim 1 in which at least two wavelengths are caused to be focused onto said small spot on said sample (SS) and are caused to be sequentially directed, by said digital light processor, into said detector (DET).

4. A system as in claim 1 which further comprises:
a second focuser (F2);
positioned between said stage (STG) for supporting a sample, and said disperser (DISP), such that said at least one wavelength in said spectroscopic beam of electromagnetic radiation which is focused onto said small spot on said sample (SS) by said first focuser (F1), reflects from said small spot on said sample (SS) and is focused onto said disperser (DISP) by said second focuser (F2).

5. A method of investigating a small spot on a sample (SS) with at least one wavelength in a beam of spectroscopic electromagnetic radiation comprising:
a) providing a system sequentially comprising:
a source (S) of a spectroscopic beam of electromagnetism;
a first focuser (F1);
a stage (STG) for supporting a sample;
provision for mounting a second focuser (F2);
a disperser (DISP);
a digital light processor (DLP);
a third focuser (F3); and
a detector (DET);
said system further comprising a computer (CMP) system for controlling the position of said first focuser (F1), and for operating said digital light processor (DLP) in synchrony therewith;
such that in use a spectroscopic beam of electromagnetic radiation is provided by said source (S) thereof and directed to pass through said first focuser (F1), interact with a small spot on a sample (SS) placed on said stage (STG) for supporting a sample (SS), reflect therefrom and then become dispersed by interaction with said disperser (DISP) before being directed onto said digital light processor (DLP);
and such that in use said computer (CMP) system causes said first focuser (F1), to be positioned at a known distance from said small spot on said sample (SS) so that at least one wavelength in said spectroscopic beam of electromagnetic radiation is focused onto said small spot and such that said computer also simultaneously operates said digital light processor (DLP) to direct said at least one wavelength, after focusing by the third focuser (F3) into said detector (DET), while diverting other wavelengths away from said detector (DET);
b) causing said source of a spectroscopic beam of electromagnetism to provide a spectroscopic beam of electromagnetism and direct it toward said first focuser (F1);
c) said computer causing said first focuser (F1) to be positioned at a known distance from said small spot on said sample (SS) so that at least one wavelength in said spectroscopic beam of electromagnetic radiation is precisely focused onto said small spot, and such that said computer also simultaneously operates said digital light processor (DLP) to direct said at least one wavelength, after focusing by said third focuser (F3), into said detector (DET), while diverting other wavelengths which are not precisely focused onto said small spot on said sample (SS) away from said detector (DET).

6. A method as in claim 5, further comprising said computer causing said first focuser (F1) to be positioned at a distance from said small spot on said sample (SS) which is different from that in said claim 5, so that at least one other wavelength in said spectroscopic beam of electromagnetic radiation is precisely focused onto said small spot on said sample (SS) by said first focuser (F1), and such that said computer also simultaneously operates said digital light processor (DLP) to direct said at least one other wavelength into said detector (DET), while diverting other wavelengths which are not precisely focused onto said small spot on said sample (SS) away from said detector (DET).

7. A method as in claim 5, in which said detector (DET) detects the intensity of the beam of electromagnetic radiation entering thereinto, and in which said computer (CMP) further comprises the capability of causing the digital light processor (DLP) to operate to direct said at least one wavelength into said detector (DET) for a length of time such that the total integrated intensity entering the detector (DET) is of at least a minimum amount.

8. A method as in claim 5 in which the system further comprises:
a second focuser (F2);
positioned between said stage (STG) for supporting a sample, and said disperser (DISP), such that said at least one wavelength in said spectroscopic beam of electromagnetic radiation which is focused onto said small spot on said sample (SS) by said first focuser (F1), reflects from said small spot on said sample (SS) and is focused into said disperser (DISP) by said second focuser (F2).

9. A system sequentially comprising:
a source (S) of a spectroscopic beam of electromagnetism;
a disperser (DISP);
a digital light processor (DLP);
a first focuser (F1);
a stage (STG) for supporting a sample;
provision for mounting a second focuser (F2);
a detector (DET);
said system further comprising a computer (CMP) system for controlling the position of said first focuser (F1), and for operating said digital light processor (DLP) in synchrony therewith;
and such that in use a spectroscopic beam of electromagnetic radiation is directed by said source (S) thereof at said disperser (DISP), and said computer (CMP) system causes said first focuser (F1) to be positioned at a known distance from a small spot on a sample (SS) placed on said stage (STG) for supporting a sample, such that at least one wavelength in said spectroscopic beam of electromagnetic radiation is directed by the digital light processor (DLP) to be focused onto said small spot on said sample (SS) by said first focuser (F1), reflect therefrom and enter said detector (DET), and such that said computer also simultaneously operates said digital light processor (DLP) to divert other wavelengths away from said first focuser (F1).

10. A system as in claim 9 which further comprises a polarization state generator (PSG) and polarization state analyzer (PSA) between said source (S) of a spectroscopic beam of electromagnetism and said stage (STG), and between said stage (STG) and said disperser (DISP), respectively, and the system is an ellipsometer or polarimeter.

11. A system as in claim 9 which further comprises:
a second focuser (F2),
positioned between said stage (STG) for supporting a sample, and said detector (DET); such that said at least one wavelength in said spectroscopic beam of electromagnetic radiation which is focused onto said small spot on said sample (SS) by said first focuser (F1) reflects from said small spot on said sample (SS) and is focused onto said detector (DET) by said second focuser (F2), while other wavelengths are diverted away.

12. A method of investigating a small spot on a sample (SS) with at least one wavelength in a beam of spectroscopic electromagnetic radiation comprising:
  a) providing a system sequentially comprising:
    a source (S) of a spectroscopic beam of electromagnetism;
    a disperser (DISP);
    a digital light processor (DLP);
    a first focuser (F1);
    a stage (STG) for supporting a sample;
    provision for mounting a second focuser (F2);
    a detector (DET);
    said system further comprising a computer (CMP) system for controlling the position of said first focuser (F1), and for operating said digital light processor (DLP) in synchrony therewith;
    and such that in use a spectroscopic beam of electromagnetic radiation is directed by said source (S) thereof at said disperser (DISP), and said computer (CMP) system causes said first focuser (F1) to be positioned at a known distance from a small spot on a sample (SS) placed on said stage (STG) for supporting a sample, such that at least one wavelength in said spectroscopic beam of electromagnetic radiation is directed by the digital light processor (DLP) to be focused onto said small spot on said sample (SS) by said first focuser (F1), reflect therefrom and enter said detector (DET), and such that said computer also simultaneously operates said digital light processor (DLP) to divert other wavelengths away from said first focuser (F1);
  b) causing said source of a spectroscopic beam of electromagnetism to provide a spectroscopic beam of electromagnetism and direct it toward said disperser (DISP), such that said spectroscopic beam is dispersed and then proceeds toward said digital light processor (DLP);
  c) said computer causing said digital light processor (DLP) to direct at least one wavelength toward said focuser (F1), while diverting other wavelengths away from said first focuser (F1), and to simultaneously cause said first focuser (F1) to be positioned at a known distance from said small spot on said sample (SS) so that said at least one wavelength in said spectroscopic beam of electromagnetic radiation is precisely focused onto said small spot on said sample (SS) by said first focuser (F1), reflect therefrom and enter said detector.

13. A method as in claim 12 which further comprises said computer causing said first focuser (F1) to be positioned at a distance from said small spot on said sample (SS) which is different from that in said claim 12, so that at least one other wavelength in said spectroscopic beam of electromagnetic radiation is directed by the digital light processor (DLP) and focused onto said small spot on said sample (SS) by said first focuser (F1), and such that said computer also simultaneously operates said digital light processor (DLP) to direct said at least one other wavelength into said first focuser (F1), while diverting other wavelengths away therefrom.

14. A method as in claim 13, in which said detector (DET) detects the intensity of the beam of electromagnetic radiation entering thereinto, and in which said computer (CMP) further comprises the capability of causing the digital light processor (DLP) to direct said at least one wavelength into said detector (DET) for a length of time such that the total integrated intensity entering the detector (DET) is of at least a minimum amount.

15. A system as in claim 12 which further comprises:
  a second focuser (F2),
  positioned between said stage (STG) for supporting a sample, and said detector (DET); such that said at least one wavelength in said spectroscopic beam of electromagnetic radiation which is focused onto said small spot on said sample (SS) by said first focuser (F1) reflects from said small spot on said sample (SS) and is focused onto said detector (DET) by said second focuser (F2), while other wavelengths are diverted away.

* * * * *